United States Patent [19]

Carlson et al.

[11] 4,067,645

[45] Jan. 10, 1978

[54] MINIMUM MEAN-SQUARE ERROR LINEAR OPTICAL FILTER

[75] Inventors: F. Paul Carlson, Seattle, Wash.; Joseph E. Ward, III, St. Paul, Minn.

[73] Assignee: The Board of Regents of the University of Washington, Seattle, Wash.

[21] Appl. No.: 644,894

[22] Filed: Dec. 29, 1975

Related U.S. Application Data

[62] Division of Ser. No. 469,376, May 13, 1974, Pat. No. 3,947,123.

[51] Int. Cl.$^2$ .......................... G02B 5/20; G02B 27/38
[52] U.S. Cl. .................................. 350/162 SF; 356/71
[58] Field of Search ........................... 350/162 SF, 3.5; 356/71

[56] References Cited

U.S. PATENT DOCUMENTS 3,501,221  3/1970  Lohmann .............................. 350/3.5

OTHER PUBLICATIONS

Horner, *Jour. of the Optical Society of America*, vol. 59, No. 5, pp. 553–558, May 1969.
Caulfield, *Applied Optics*, vol. 13, No. 5, May 1974, pp. 996–997.
Vander Lugt, *Optica Acta*, vol. 15, No. 1, pp. 1–33, Feb. 1968.

*Primary Examiner*—Ronald J. Stern
*Attorney, Agent, or Firm*—Christensen, O'Connor, Garrison & Havelka

[57] ABSTRACT

A method of forming a minimum mean-square error linear filter photographically is disclosed.

The optimum filter may be obtained photographically. In one form, a first photographic negative of a monolayer of cells having a high percentage of cells of the given type is made at the focal plane of a transforming lens mounted so as to collect the light scattered by the monolayer; and, developed for a gamma of unity. Thereafter, a second photographic negative is made at the same focal plane of a monolayer of cells containing a normal percentage of cells of the given type using the first negative as a filter. The second negative is developed for a gamma of two. The resulting photographic plate is a realization of the desired optimum (minimum mean-square error linear) filter. Alternatively, a sandwich of two photographic plates, one positive and obtained from a monolayer of cells having a high percentage of cells of the given type and the other negative obtained from a monolayer of cells having a normal percentage of cells of the given type, is constructed to provide a physical realization of the desired optimum filter.

6 Claims, 3 Drawing Figures

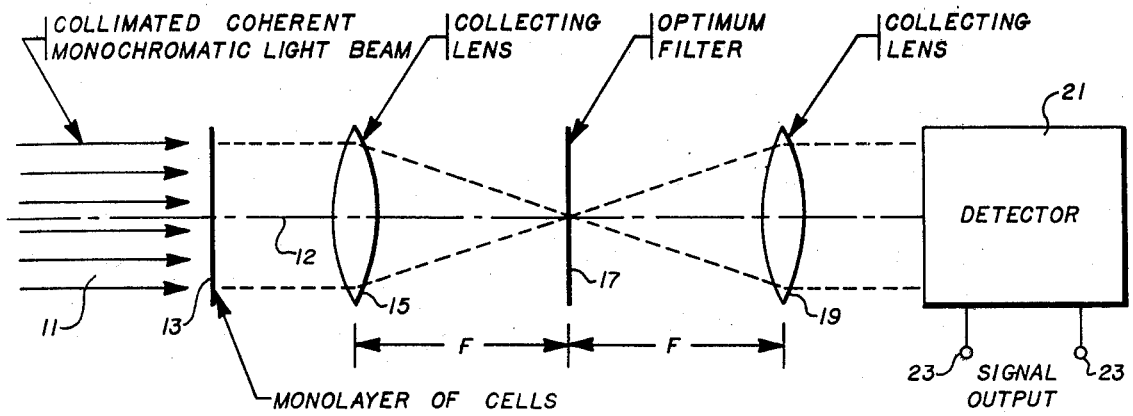

MINIMUM MEAN-SQUARE ERROR LINEAR OPTICAL FILTER

This is a divisional of application Ser. No. 469,376, filed May 13, 1974, now U.S. Pat. No. 394,7123.

BACKGROUND OF THE INVENTION

This invention is directed to particle identification and more particularly, to the identification of particles of one type located in a mass or ensemble of particles of various types, and the counting of the identified particles, if desired.

The herein described invention was developed for use in identifying and counting the number of biological cells of a given type present in a mass of cells of varying types and is described in that environment. In particular, the invention was developed for use in determining the percentage of reticulated (immature) blood cells, commonly called reticulocytes, present in a blood specimen. However, it will be appreciated from the following description that the invention has much broader applicability. For example, it can be utilized merely to identify cells or it can be used to identify and, if desired, count the number of biological cells of other types (such as leukocytes, platelets, and erythrocytes, etc.). Further, the invention can be utilized in pap smear analysis, and in other cancer screening operations.

The invention is also applicable to the identification and counting of particles other than biological cells. Further, the invention is useful in areas other than detecting defects of undesired (or desired) foreign bodies contained in a support medium. Hence, the use of the invention should not be construed as limited to the particular biological cell environment hereinafter described.

In recent years, various attempts have been made to develop methods of and apparatus for automatically identifying and counting biological cells and, in particular, the various biological cells contained in blood. For the most part, such attempts have been directed toward the identification and counting of leukocytes, although some attention has been given to the identification and counting of reticulocytes as well. In general, prior art attempts have been directed to the development of instruments for automatically analyzing blood cell images in a topographic manner. One prior art apparatus uses a high resolution microscope to magnify a conventionally stained blood smear illuminated by monochromatic light. A scanning detector such as a vidicon tube scans the magnified image. The output of the scanning detector is analyzed by a special purpose computer, or a suitably programmed general purpose computer, to provide the desired information. More specifically, the topology data contained in the scanning detector signal is sorted and analyzed by a series of algorithms to provide the desired information. Obviously, this apparatus is expensive and the method involved is time consuming, even considering the capabilities of modern digital computers. Moreover, highly skilled individuals are required to prepare the required program, if a general purpose digital computer is used. Further, a highly skilled medical technologist is still required to classify abnormal cells which the computer fails to recognize.

Another prior art proposal for identifying biological cells involves the suspension of the cells in a liquid. The suspended cells are carried through a flow tube where they interact with a focused laser beam. Information derived from the detection of the scattered light is analyzed by a suitable special purpose computer, or programmed general purpose computer. This approach is, obviously, also expensive and time consuming. First, the biological cells must be liquid suspended and, then they must be treated with a suitable material so that the flourescent properties of the cells to be detected are adequately enhanced. Finally, the material must be analyzed by expensive electronic equipment.

Another prior art biological cell identification and counting apparatus includes a continuous flow autoanalyzer. Cell identification is accomplished by spectrophotometrically analyzing differential cytochemical reactions, and by cell sizing. Again, this apparatus is expensive and its use is time consuming.

In general, the foregoing (except for the automatic microscope) and most other prior art methods and apparatus ignore the morphology (geometry) of the cells being analyzed. Rather, other cells parameters are emphasized, such as the interaction of a desired type of cell with a certain chemical or chemicals. The present invention, on the other hand, as will be better understood from the following description, places its main emphasis on cell morphology.

It will be appreciated from the foregoing brief discussion that the prior art apparatus for identifying and counting biological cells is expensive. In addition, the methods used are time consuming. Further, these methods and apparatus require the skill of highly trained personnel. Moreover, many of the prior art methods and apparatus are unsuitable for use in certain environments, such as the identification and counting of reticulocytes.

In view of the expensive nature of the prior art apparatus and their unsuitability in many environments, classical manual techniques for identifying and counting biological cells remains widespread. In the particular case of reticulocytes, the classical techniques involve incubating a few drops of blood with a suprevital stain (such as Methylene Blue). Thereafter, thin smears are prepared and, by light microscopy, the number of reticulocytes among a predetermined number of red cells (such as 1,000 or 5,000) are manually counted. The end result is a percentage number representing the percentage of red blood cells that are reticulated. Not only is this technique tedious and time consuming, but it is also limited in accuracy. A recent study by the National Communicable Disease Center showed that performance was unsatisfactory in 40% of the laboratories tested with respect to the differential classification of blood cells on normal blood smears, and unsatisfactory in an even greater percent of the laboratories when the test specimens were blood smears from certain frequently encountered abnormal conditions. Thus, it is desirable to provide a method of and an apparatus for achieving the desired information without requiring such tedious and time consuming labor, along with equal to or better accuracy, not only for use in identifying and counting reticulocytes, but also for use in identifying and counting other types of biological cells and particles.

Therefore, it is an object of this invention to provide a method of and an apparatus for identifying the particle or particles of a given type located in an ensemble of particles of varying types.

It is a further object of this invention to provide a method of and an apparatus for identifying the particle or particles of a given type located in a ensemble of particles of varying types and either counting the particles or determining their concentration with respect to particles of some other given type.

It is also an object of this invention to provide a method of and an apparatus for identifying and counting the biological cells of a given type present in a mixture ensemble of biological cells of various types.

It is another object of this invention to provide a method of and an apparatus for determining the percentage of reticulated red blood cells present in a blood specimen.

It is a further object of this invention to provide an inexpensive apparatus suitable for rapidly identifying and counting the number of particles of a given type present in an ensemble of particles of various types.

It is yet another object of this invention to provide an inexpensive apparatus suitable for rapidly identifying and counting the number of biological cells of one type in an ensemble of biological cells of varying types, and in particular the number of reticulated red blood cells in a blood specimen.

During the development of the main method and apparatus of the present invention, it was found necessary to produce an optical filter having a minimum mean-square error linear characteristics. Thus, it is a subsidiary object of this invention to provide a method of producing a minimum mean-square error linear optical filter, and the filter obtained thereby.

SUMMARY OF THE INVENTION

In accordance with principles of this invention, a method of identifying and counting, if desired, the number of particles of a given type located in an ensemble of particles of various types provided. In general, the method comprises the steps of; preparing a monolayer of the ensemble of particles or cells to be analyzed; directing a coherent monochromatic electromagnetic wave energy beam toward said monolayer; collecting the electromagnetic wave energy scattered by said monolayer of said particles or cells; and, passing the collected scattered electromagnetic wave energy through a minimum mean-square error linear filter positioned so as to suppress the electromagnetic wave energy scattered by the particles or cells other than the given particles or cells and, thereby, enhance the electromagnetic wave energy scattered by the given particles of cells.

In accordance with other principles of this invention, the method comprises the further steps of: collecting the filtered electromagnetic wave energy; and, integrating and squaring the filtered, collected electromagnetic wave energy.

In accordance with yet other principles of this invention, the electromagnetic wave energy beam is a coherent monochromatic light beam.

In accordance with further principles of this invention, methods of producing minimum mean-square error linear filters are provided. In one form, the method comprises the steps of: directing a monochromatic electromagnetic wave energy beam such as a light beam toward a first monolayer of particles or cells having a high percentage of particles or cells of the given type; collecting the light scattered by said first monolayer with a transform lens; taking a first photograph at the focal plane of the transform lens to obtain a negative of the scattered light intensity; directing a monochromatic light beam toward a second monolayer of particles or cells having a normal population of particles or cells of the given type; collecting the light scattered by said monolayer with a transform lens; and, taking a second photograph at the focal plane of the transform lens using the first photograph as a filter. The second photograph forms the desired minimum mean-square error linear filter. In an alternate form, the inventive method of obtaining an optimum filter generally comprises the steps of: obtaining a photographic positive of the monochromatic light scattered by a first monolayer of an ensemble of particles or cells having a high percentage of particles or cells of the given type; obtaining a photographic negative of the monochromatic light scattered by a second monolayer of an ensemble of particles or cells including a normal population of particles or cells of the given type; and, sandwiching the photographic positive plate with the photographic negative.

In accordance with further principles of this invention, the methods utilized to obtain the desired mean-square error linear filter both include the substeps of: developing the photograph related to the high percentage monolayer at a gamma of one; and, developing the photograph related to the normal percentage monolayer at a gamma of two.

In accordance with further principles of this invention, an apparatus for identifying and counting particles of a given type located in an ensemble of particles of various types is provided. The apparatus comprises: a monochromatic source of coherent electromagnetic wave energy; support means for supporting a monolayer of particles in the beam generated by the monochromatic source of coherent electromagnetic wave energy; a lens for collecting the electromagnetic wave energy scattered by the monolayer of particles; and, an optimum filter located in the focal plane of the lens, the optimum filter being adapted to suppress electromagnetic wave energy scattered by particles other than the given type.

In accordance with further principles of this invention, the cptimum filter is a minimum mean-square error linear filter.

In accordance with still further principles of this invention, one mathematical form of the optimum filter is given by the following equation:

$$H(\omega) = \frac{S_{ss}(\omega)}{S_{ss}(\omega) + S_{nn}(\omega)}$$

where:

$S_{ss}(\omega)$ = Fourier power spectral density of the light scattered by particles of the given type (signal)

$S_{nn}(\omega)$ = Fourier power spectral density of the light scattered by particles of all types but the given type (noise).

In accordance with still further principles of this invention, second lens is located on the remote side of the filter and collects the filtered light. Located on the remote side of the second lens is an integrating and squaring detector. The output of the detector is, preferably, an electrical signal that contains information related to the number of given particles in the monolayer.

It will be appreciated from the foregoing description that the invention provides an uncomplicated method of and an apparatus for detecting the magnitude of a given particle type in an ensemble of particles of various types. The particles may be, for example, biological cells, such as reticulocytes. Alternatively, other types of particles can be identified utilizing the invention. In any event, the invention utilizes the known fact that the farfield diffraction pattern (in the focal plane of a lens) is in the form of a two-dimensional Fourier transform. This phenomena is exploited by the invention to identify cells or particles of a given type. More specifically, the invention uses an optical data-processing system employing an optimum filter to weigh the Fourier spectrum of the cells or particles in a manner such that light scattered by particles other than the given type are suppressed whereby light scattered by the given particle or particles are enhanced (relatively). The population density of the given type is determined by optically integrating the thusly enhanced image. The resultant information can be turned into a percentage value by determining the population density of cells or particles of another type and comparing the derived information. In the event that the population density of a particular type is approximately constant from sample to sample, a percentage relative to this particular type can be obtained by simple calibration.

It will also be appreciated from the foregoing description that while film filters have been described other types of filters can be utilized by the apparatus of the invention. For example, dichromated gelatin holograms or photo dichroics can be used. In general, all that is necessary is that the filters have controlled opacity to the electromagnetic wave energy being used. It will further be appreciated that the monolayer of cells or particles can be moving as well as stationary. In fact single cells can be directed through the coherent monochromatic electromagnetic wave energy beam, if desired.

BRIEF DESCRIPTION OF THE DRAWINGS

The foregoing objects and many of the attendant advantages of this invention will become more easily appreciated as the same becomes better understood from the following detailed description when taken in conjunction with the accompanying drawings wherein:

FIG. 1 is a schematic diagram of a preferred embodiment of an apparatus formed in accordance with the invention;

FIG. 2 is a schematic diagram of a first process for forming an optimum filter suitable for use in the embodiment of the invention illustrated in FIG. 1; and, FIG. 3 is a schematic diagram of an alternate process for forming an optimum filter suitable for use in the embodiment of the invention illustrated in FIG. 1.

DESCRIPTION OF THE PREFERRED EMBODIMENT

General Introductory Description

As generally illustrated in FIG. 1, in accordance with the invention, a collimated coherent monochromatic light beam 11 (electromagnetic wave energy) is intersected by a monolayer of cells 13. Preferably, the coherent monochromatic light beam is generated by a laser and collimated by a collimating lens. The monolayer of cells 13 lies in a plane located orthogonal to the axis 12 defined by the collimated light beam 11 and includes a cell or cells of the type (given type) to be identified and counted, if desired, located in an ensemble of cells of various types. For example, the monolayer may be a blood smear and include reticulocytes (immature red blood cells) randomly located among erythrocytes, leukocytes, platelets and other artifact normally contained in a blood smear. The blood smear may be mounted on a glass slide, for example.

The monolayer of cells 13 scatters the collimated coherent monochromatic light beam and the thusly scattered light is collected by a first collecting lens 15. The first collecting lens is centered on the main optical axis 12 and directs the scattered light toward an optimum filter 17. The optimum filter is also centered on the main optical axis 12. In addition, the optimum filter is located at the focal plane of the first collecting lens 15. The optimum filter, as will be better understood from the following description, suppresses the light scattered by all of the cells contained in the monolayer, except the light scattered by the reticulocytes (the given type to be identified and counted) whereby the light scattered by the reticulocytes is enhanced (relatively). The light passed by the optimum filter 17 is collected by a second collecting lens 19 centered about the main optical axis 12 and located a focal length (F) from the "output" side of the optimum filter 17. The second collecting lens 19 directs the "passed" light onto the light sensitive surface of a light detector 21. In accordance with its input, the light detector generates an output signal at a pair of output terminals 23 suitable for connection to an indicator (not shown), such as a meter. If desired, automatic means may be provided for moving suitably supported monolayers into and out of the main optical axis 12. Preferably, the lenses and filter bandwidths are designed to maximize the available bandwidth in the focal plane corresponding to the domain of reticulum and cell sizes.

While FIG. 1 illustrates a monolayer of cells mounted on a glass slide located at a fixed position, for example, it will be appreciated that the monolayer could be moved through the optical axis 12, if desired. In fact cells could be passed through the axis one-at-a-time, if desired. Moreover, the monolayer could be located between the first collecting lens 15 and the optimum filter 17, rather than in the collimated beam 11. If located in such a position, movement of the monolayer back and forth between the first collecting lens 15 and the optimum filter will provide a scaling benefit.

OPTIMUM FILTER THEORY

In analogy with a communication system, all cells on the blood slide together with artifact are considered to be a combination of signal and noise. The particular cell type (reticulocytes) to be identified and counted form a "signal" ($s$); and, the remaining cells and artifact represent "noise" ($n$). Thus, the light ($x$) scattered by the monolayer 13, collected by the first collecting lens 15 and received by the optimum filter 17 can be represented by the following equation:

$$x = s + n \quad (1)$$

The optimum filter of the invention, thus, must optimally distinguish the signal from the noise. There is, however, a constraint on optimization; specifically, the mean-square error that exists between the signal estimated to be present, and the actual signal present. If the estimated signal is denoted $\hat{s}$, it can be represented mathematically by a convolution of the input signal $x(u)$ and the desired filter impulse response $h(u)$. The following equation describes this convolution:

$$\hat{s}(u) = \int_{-\infty}^{\infty} x(u-\alpha) h(\alpha) \, d\alpha \qquad (2)$$

The statistical expectation value of the squared error can be represented by the following expression:

$$E[|\hat{s} - s|^2] \qquad (3)$$

where: E is the expectation operator; and, the $\hat{s}$ and s terms are defined above, This expression then is the one to be minimized.

The solution to this minimization problem, which provides an optimum estimate satisfying equation (2), is given by the Weiner-Kolmogorov theory. In accordance with the theory, the mean-square error is minimized when the error is orthogonal to the data, i.e., $$E[(\hat{s} - S) \cdot x] = 0. \qquad (4)$$

Expanding equation (4) in terms of equations (1) and (2) yields the following equation:

$$R_{sx}(\tau) = \int_{-\infty}^{\infty} R_{xx}(\tau - \alpha) h(\alpha) \, d\alpha, \qquad (5)$$

where $R_{xx}(\tau)$ is the auto-correlation function of the signal $x$.

This result simplifies when the signal and noise are uncorrelated. In this case equation (5) reduces to $$R_{ss}(\tau) = \int_{-\infty}^{\infty} [R_{ss}(\tau - \alpha) + R_{nn}(\tau - \alpha)] h(\alpha) \, d\alpha. \qquad (6)$$

Taking the Fourier transform of equation (6) and solving for $H(\omega)$ results in the production of the filter equation:

$$H(\omega) = \frac{S_{ss}(\omega)}{S_{ss}(\omega) + S_{nn}(\omega)}. \qquad (7)$$

Where:
$H(\omega)$ is the desired frequency response of the filter;
$S_{ss}(\omega)$ is the power spectral density (Fourier transform squared) signal; and,
$S_{nn}(\omega)$ is the power spectral density (Fourier transform squared) noise.

In accordance with the invention, a coherent optical data processor (optical filter) is used to perform the desired filtering operation in the frequency domain (focal plane) of a lens. Procedures for realizing an optical filter having the mathematical characteristics denoted in equation (7) are presented next.

OPTIMUM FILTER REALIZATION

In accordance with the invention, two different methods of obtaining or realizing an optical filter having the characteristics described mathematically in equation (7) are provided. In either case, it is necessary to obtain a monolayer having a high percentage of the given cell (reticulocytes), and a monolayer having a normal population of the given cell.

Two of the various methods that may be utilized to obtain monolayers having high reticulocyte populations are hereinafter described. In the first method, a standard blood sample is first centrifuged to take advantage of the well known fact that reticulocytes are less dense than are mature erythrocytes. Thus, a two to three-fold concentration of reticulocytes is formed in the upper layer of the centrifuged blood sample. A sample is then taken from the upper layer of cells. By this technique, samples with reticulocyte counts as high as 30–50% of the total red blood cell count can be obtained from samples with original reticulocyte counts of 10–20%. Because this reticulocyte count is still not exceedingly high, the second method of obtaining a high concentraton of reticulocytes is preferred.

The second method comprises injecting subcutaneously a suitable animal, such as a rabbit, with 0.5 cc/kg of a 2.5% solution of phenylhydrazine for four days. This injection causes a severe hemolytic anemia condition to occur. By the seventh day after the injections are started, the blood of the animal has a reticulocyte count of greater than 90%. Blood samples are taken from the animal as it recovers, at one-two day intervals. In this manner, an array of reticulocyte counts that range from 75% or more down to around 5% are obtained. Thus, not only are samples having high reticulocyte counts obtained by this technique, but samples having varying reticulocyte counts are also obtained. Variations in average sizes due to different animal blood are accounted for by the adjustment of focal lengths during filter formation.

The obtained blood samples are then stained with new methylene blue and smears are made on counterslip glass slides with a suitable centrifuge. This technique provides a uniform monolayer of cells on the slide. The slides may be counterstained with Wright's stain to provide more contrast between the reticulocytes and the remainder of the red blood cells, although this is not necessary. In this manner, a monolayer of cells having a high percentage of reticulocytes is obtained. As will be better understood from the following description, such a slide, and a slide having normal population of reticulocytes, are used to create the desired optimum filter.

In accordance with the invention, the optimum filter 17 is created by photographing the Fourier spectrum of both a high count slide and a normal count slide at the focal plane of a transform lens. The method takes advantage of the well known fact that the amplitude transmission coefficient, $t_a$, of a film can be represented by the following equation:

$$t_a = C_o I^{-\gamma/2}, \qquad (8)$$

where: I is the incident illuminating intensity; $C_o$ is an appropriate constant for the particular film being used (C is a constant in all of the following equations); and, $\gamma$ is the gamma of the film or the slope of the Hurter-Driffield curve. As is well-known in the photographic art, the gamma factor may be adjusted by a suitable choice of film and development procedures.

In accordance with the invention, two different photographic methods can be employed to produce the desired optimum filter. FIG. 2 is a schematic illustration of one method, and FIG. 3 is a schematic illustration of the second method. In the first method, a photographic negative is made of the Fourier spectrum of a slide having a high reticulocyte count, the slide being illuminated by coherent monochromatic light of the type emitted by a laser. This negative represents the signal spectrum and is used as a filter for a second photographic negative taken of the Fourier spectrum of a slide having a normal reticulocyte count (signal plus noise). The second negative forms the desired optimum filter. Both photographs are taken at the focal plane of a transform lens, and the first is developed at a gamma of one and the second is developed at a gamma of two. In order to better understand the formation of the optimum filter using the first method, the following mathematic description is provided.

The incident illuminating intensity, $I_1$, for a high count slide is the signal spectrum, $S_{ss}(\omega)$. Thus, for $\gamma = 1$, equation (8) can be written as:

$$t_{a1} = C_1 S_{ss}(\omega)^{-\frac{1}{2}} \qquad (9)$$

Since amplitude transmission, $t_a$, can be considered the square root of an intensity transmission coefficient $\tau$, equation (9) can be rewritten in terms of an intensity coefficient as:

$$\tau_1 = \frac{C_2}{S_{ss}(\omega)} \qquad (10)$$

Thus, the first negative possesses an intensity transmission coefficient related to signal only, ignoring minor errors that exist because a perfect 100% reticulocyte count slide cannot presently be obtained.

As discussed above, the first negative is used to filter light impinging on a second negative located so as to photograph the Fourier spectrum of a slide having a normal population of reticulocytes (signal plus noise). Thus, the incident illuminating intensity, $I_2$, impinging on the second photographic negative is the product of the intensity transmission coefficient $\tau_1$ and the incident illuminating signal plus noise intensity. In other words, the incident illuminating intensity, $I_2$, can be represented by the following equation:

$$I_2 = C_3[S_{ss}(\omega)^{-1}][S_{ss}(\omega) + S_{nn}(\omega)] \qquad (11)$$

If the gamma of the second plate is adjusted to 2, then the second amplitude transmission coefficient $t_{a2}$, can be represented by the following equation:

$$t_{a2} = C_4 \left[ \frac{S_{ss}(\omega) + S_{nn}(\omega)}{S_{ss}(\omega)} \right]^{-2/2} = \frac{C_4 S_{ss}(\omega)}{S_{ss}(\omega) + S_{nn}(\omega)} \qquad (12)$$

Comparison of equation (12) with equation (7) reveals that the amplitude transmission coefficient of the second negative is the same as the desired filter function. Thus, the second photographic plate forms the desired optimum filter without requiring further processing.

In the foregoing manner, an optimum filter having minimum mean-square error linear filtering characteristics is created. It will be appreciated by those skilled in the communication art that the filter function complies with Weiner-Kolmgorov filter theory. When this filter is placed in at the Fourier transform plane of a collecting lens, as illustrated in FIG. 1, light scattered by cells (or particles) having different geometric characteristics or morphology than the geometric characteristics of the desired cells is suppressed, whereby the light scattered by the desired cells is enhanced in a relative manner.

It will be appreciated from the foregoing disscussion that the invention utilizes the known fact that the far-field diffraction pattern (in the focal plane of a lens) is in the form of a two-dimensional Fourier transform. The optimum filter in essence weighs the Fourier spectrum created by the scattered light so as to enhance the light related to particular (given) cell types while suppressing light scattered by other types in a relative manner. As will be better understood from the following description, the population density (count) of cells of the given type may be determined directly by optically integrating the enhanced cell image.

ALTERNATE METHOD OF OPTIMUM FILTER REALIZATION

FIG. 3 illustrates the alternate method of obtaining or realizing an optimum filter of the desired type. In this case, two photographic negatives are separately exposed, again at the focal plane of a transform lens and using coherent monochromatic light. The first negative is exposed to the light scattered by a monolayer having a high count of the given cell type (reticulocytes). This negative is developed for a gamma of one and used to create a photographic positive. The second negative is exposed to a monolayer having a normal count of cells of the given type and developed for a gamma of two. The photographic positive made from the first negative is then sandwiched with the second negative. The result is the desired optimum filter. In certain instances, the second method of realizing an optimum filter may have certain beneficial advantages since control of the relative exposures is slightly better.

It will be appreciated by those skilled in the art that the two described optical filters are not the only filters that can be used by the invention. For example, dichromated gelatin holograms could be used; or, photo dichroics. In general all that is necessary is that the filter medium be such that its opacity can be controlled in a manner such that the desired filter characteristics can be created.

RETICULOCYTE SIGNAL SPECTRUM

It can be mathematically demonstrated that the signal spectrum of a reticulocyte is composed of three components: (1) a convolution between the spectrum due to the enlarged red cells and the spectrum due to reticulum which accounts for the localization of reticulum within the reticulated red cells; (2) the power spectrum due to the enlarged red cells alone and the reticulum alone which account for their characteristic sizes and shapes; and, (3) a delta function (DC term) contributing only to the power at the origin. In accordance with the invention, the latter component (3), is removed by placing a stop, approximately 1/10 the diameter of the central Airy disc for the red cells, at the origin of the filter. If this stop is not included, this term, obviously, would dominate the resultant image and, thus, make the light scattered by the reticulocytes more difficult to detect.

With respect to the other two components, (1) and (2), the minimum mean-square error linear filter optimally passes the reticulocyte or signal spectrum while suppressing the spectrum of other cells. In other words, the optimum filter recognizes (passes light related to) only those red blood cells containing reticulum within their boundaries and ignores (suppresses light related to) artifact and cells not containing reticulum.

The effect of reticulum within a cell is to broaden the cell's spectrum over a wider frequency range. This spectrum broadening is due to the convolution process. Thus, the most important of the three components is the convolution component.

OUTPUT INFORMATION

As previously discussed with respect to FIG. 1, the light "output" of the second filter may be collected by a second collecting lens 19 and imaged onto the photosensitive surface of a photodetector 21. The output of the detector can be applied to an electric meter, for example. Obviously, the method of the invention can be practiced, and the apparatus used, by relatively unskilled individuals.

In many instances, particularly in the area of reticulocyte identification and counting, it is desirable to relate the output of the detector to some other value in order to provide percentage information. In the particular case of reticulocytes, the other value is the total number of erythrocytes in the monolayer being investigated. As will be better understood from the following discussion, the basic inventive apparatus is easily modified to provide this desired result.

Since the reticulated cell signal spectrum $S_{ss}(\omega)$, has the morphological information pertaining to the host cell (erythrocytes), a portion of the signal $S_{ss}(\omega)$ is related to erythrocyte structure. This information is used to measure the total number of erthrocytes present in any given signal spectrum. More specifically, in accordance with the invention, a minimum meansquare error linear filter is used to provide a total cell count. The total cell count is used for percentage calibration purposes. Alternatively, the output can be normalized to total erythrocyte density, if desired.

EXAMPLE OF AN ACTUAL EMBODIMENT

In one actual embodiment of the invention, a helium-neon 5-mW laser beam 1 mm in diameter was expanded with a 10 power objective and a 25-$\mu$ pinhole spatial filter. The resultant diverging beam was approximately both spatially and temporally coherent. The light was then collimated with a 100 mm f/2 lens to obtain a collimated beam about 20 mm in diameter. This beam was used to illuminate an entire blood slide. A first 80 mm collecting lens then formed the Fourier transform in its focal plane. This transform was optically weighted (filtered) by an optimum filter of the type previously described and a second 80 mm collecting lens collected the enhanced image of the reticulocytes present on the input slide, and projected it onto a ground glass plate behind which a silicon photocell was mounted. The spacing between all elements in the system was the focal length, 80 mm, of the lenses to minimize Fourier transformation phase distortion.

CONCLUSION

It will be appreciated from the foregoing description that the invention provides a method of and an apparatus for recognizing and, if desired, counting particles of one type randomly located in an ensemble of particles of varying types. The method of the invention generally comprises the steps of: directing a coherent monochromatic electromagnetic wave (light) beam, such as that generated by a laser, toward a monolayer of particles located in a plane orthogonal to the axis of the light beam so that the monolayer of particles scatters the incoming light in accordance with the morphological characteristics of the various particles; collecting the scattered light in the farfield diffraction zone with a collecting lens; and, filtering the collected light with an optimum filter located at the focal plane of the collecting lens. The optimum filter eliminates the DC component along the beam axis and suppresses undesired light i.e., that scattered by particles other than a given type of particle. Thus, in a relative manner light scattered by the given type of particles is enhanced. In accordance with further method steps, the "enhanced" light is collected and imaged onto a suitable detecting device. In one form, the detecting device integrates and squares its received light to provide an output signal directly related to the number of particles of the desired type located in the ensemble particles. The particles may be biological cells or any other type of particles or items whose morphological characteristics allow them to scatter light (or other forms of electromagnetic wave energy).

The method of the invention can be utilized to identify a particular particle or cell, or can be used to count a plurality of particles or cells, of a given type. The particles or cells can be stationary in the beam or moving therethrough. Moreover, they can be located in a collimated portion of the beam or a converging portion. Being located in the converging portion allows the resultant image to be "scaled".

The apparatus for carrying out the invention is equally uncomplicated and is suitable for use by relatively unskilled technicians. Specifically, the apparatus of the invention comprises a source of coherent light, such as a laser beam. Mounted in the laser beam, at right angles to the optical axis thereof, is a slide containing a monolayer of cells to be analyzed. The monolayer scatters the light beam and the scattered light is collected by a collecting lens. The collecting lens images the collected light onto a minimum mean-square error linear filter located at its focal plane. The minimum mean-square error linear filter suppresses the light scattered by cells other than a given type and, thereby, enhances the light scattered by cells of the given type. The "output" of the filter is detected and analyzed to provide an electronic signal related to the desired information. It will be appreciated that no microscope or other complicated mechanical or electromechanical system, or sophisticated chemical processing system, is needed by the invention.

In addition to the basic method and apparatus of the invention, it also provides an uncomplicated method of realizing an optical Weiner-Kolmogorov filter. Specifically, the invention merely requires two optical imaging steps and certain conventional photographic developing steps to obtain a filter of the desired type. The filter can be made up of a single photographic plate or a sandwich of two photographic plates, as desired.

It will be appreciated from the foregoing description that while preferred embodiments of the invention have been illustrated and described, various changes can be made therein without departing from the spirit and scope of the invention. Hence, the invention can be practiced otherwise than as specifically described herein.

The embodiments of the invention in which an exclusive property or privilege is claimed are defined as follows:

What is claimed is:

1. A method of forming a minimum mean-square error linear optical filter having the following mathematical amplitude frequency response:

$$H(\omega) = \frac{S_{ss}(\omega)}{S_{ss}(\omega) + S_{nn}(\omega)}$$

where:

$S_{ss}(\omega)$ is the power spectral density of the signal to be enhanced by the minimum mean-square linear optical filter; and, $S_{nn}(\omega)$ is the power spectral density of the signal to be suppressed by the minimum mean-square linear optical filter, said method comprising the steps of:

directing a beam of coherent monochromatic light toward a monolayer of particles having a high percentage of particles having the power spectral density $S_{ss}(\omega)$;

collecting the light scattered by said particles with a transforming lens;

making a first photographic negative of the scattered light collected by said transforming lens at the focal plane of said transforming lens;

developing said first photographic negative for a gamma of one;

directing a beam of coherent monochromatic light toward a monolayer of particles having the power spectral density $S_{ss}(\omega) + S_{nn}(\omega)$;

collecting the light scattered by said monolayer with a transforming lens;

making a second photographic negative of the light collected by said transforming lens at the focal plane of said transforming lens using said first photographic negative as a filter; and, developing said second photographic negative for a gamma of two.

2. A minimum mean-square error linear optical filter formed in accordance with the process recited in claim 1.

3. A method of forming a minimum mean-square error linear optical filter having the following mathematical amplitude frequency response;

$$H(\omega) = \frac{S_{ss}(\omega)}{S_{ss}(\omega) + S_{nn}(\omega)}$$

where:

$S_{ss}(\omega)$ is the power spectral density of the signal to be enhanced by the minimum mean-square error linear optical filter; and, $S_{nn}(\omega)$ is the power spectral density of the signal to be suppressed by the minimum mean-square error linear optical filter, said method comprising the steps of:

directing a beam of coherent monochromatic light toward a monolayer of particles having a high percentage of particles having the power spectral density $S_{ss}(\omega)$;

collecting the light scattered by said particles with a transforming lens;

making a first photographic negative of the scattered light collected by said transforming lens at the focal plane of said transforming lens;

developing said first photographic negative for a gamma of one;

obtaining a photographic positive from said first photographic negative;

directing a beam of coherent monochromatic light toward a monolayer of particles having the power spectral density $S_{ss}(\omega) + S_{nn}(\omega)$;

collecting the light scattered by said monolayer with a transforming lens;

making a second photographic negative of the light collected by said transforming lens at the focal plane of said transforming lens;

developing said second photographic negative for a gamma of two; and, sandwiching said photographic positive and said second photographic negative together.

4. A minimum mean-square error linear optical filter formed in accordance with the process recited in claim 3.

5. A minimum mean-square error linear optical filter having the amplitude frequency transfer function:

$$H(\omega) = \frac{S_{ss}(\omega)}{S_{ss}(\omega) + S_{nn}(\omega)}$$

where:

$S_{ss}(\omega)$ is the power spectral density of a desired optical signal; and, $S_{nn}(\omega)$ is the power spectral density of the remainder of the optical signal, said minimum mean-square linear optical filter formed in a photographic plate prepared in accordance with a process comprising the steps of:

directing a beam of coherent monochromatic light toward a monolayer of particles having a high percentage of particles having the power spectral density $S_{ss}(\omega)$;

collecting the light scattered by said particles with a transforming lens;

making a first photographic negative of the scattered light collected by said transforming lens at the focal plane of said transforming lens;

developing said first photographic negative for a gamma of one;

directing a beam of coherent monochromatic light toward a monolayer of particles having the power spectral density $S_{ss}(\omega) + S_{nn}(\omega)$;

collecting the light scattered by said monolayer with a transforming lens;

making a second photographic negative of the light collected by said transforming lens at the focal plane of said transforming lens using said first photographic negative as a filter; and, developing said second photographic negative for a gamma of two.

6. A minimum mean-square error linear optical filter having the amplitude frequency transfer function:

$$H(\omega) = \frac{S_{ss}(\omega)}{S_{ss}(\omega) + S_{nn}(\omega)}$$

where:

$S_{ss}(\omega)$ is the power spectral density of a desired optical signal; and, $S_{nn}(\omega)$ is the power spectral density of the remainder of the optical signal, said minimum mean-square linear optical filter contained in a photographic plate formed of a sandwich of a photographic positive having the transfer function $S_{ss}(\omega)$ and a photographic negative having the transfer function $S_{ss}(\omega) + S_{nn}(\omega)$ prepared in accordance with a process comprising the steps of:

directing a beam of coherent monochromatic light toward a monolayer of particles having a high percentage of particles having the power spectral density $S_{ss}(\omega)$;

collecting the light scattered by said particles with a transforming lens;

developing said first photographic negative for a gamma of one;

obtaining a photographic positive from said first photographic negative;

directing a beam of coherent monochromatic light toward a monolayer of particles having the power spectral density $S_{ss}(\omega) + S_{nn}(\omega)$;

collecting the light scattered by said monolayer with a transforming lens;

making a second photographic negative of the light collected by said transforming lens at the focal plane of said transforming lens;

developing said second photographic negative for a gamma of two; and, sandwiching said photographic positive and said second photographic negative together.

* * * * *